United States Patent [19]

Ferro

[11] Patent Number: 4,707,293
[45] Date of Patent: Nov. 17, 1987

[54] DETERGENT COMPOSITION

[75] Inventor: Antonio Ferro, Lugano Svizzera, Italy

[73] Assignee: Crinos International, Lugano, Switzerland

[21] Appl. No.: 917,293

[22] Filed: Oct. 8, 1986

Related U.S. Application Data

[63] Continuation of Ser. No. 709,508, Mar. 8, 1985, abandoned, which is a continuation-in-part of Ser. No. 628,149, Jul. 5, 1984, abandoned.

[30] Foreign Application Priority Data

Mar. 5, 1984 [IT] Italy ............................ 19898 A/84
Feb. 13, 1985 [IT] Italy ............................ 19490 A/85

[51] Int. Cl.$^4$ ............................................. C11D 3/22
[52] U.S. Cl. ........................... 252/174.17; 252/162; 252/170; 252/174.25; 252/351; 252/DIG. 5; 252/DIG. 13; 424/70; 514/846; 514/904; 514/944; 514/942; 514/943
[58] Field of Search ......... 252/107, 153, 170, DIG. 5, 252/162, 174.15, 174.17; 424/70, 168, 171, 172; 514/846, 904, 940, 941, 942, 943, 944

[56] References Cited

U.S. PATENT DOCUMENTS

| | | | |
|---|---|---|---|
| 3,277,013 | 10/1966 | Gianladis | 252/DIG. 5 |
| 3,536,816 | 10/1970 | Kellner | 514/943 |
| 3,795,624 | 3/1974 | Feinstone | 252/DIG. 5 |
| 3,952,099 | 4/1976 | Smith | 514/152 |
| 4,035,514 | 7/1977 | Davis | 252/DIG. 5 |
| 4,259,202 | 3/1981 | Tanaka et al. | 252/174.17 |
| 4,323,468 | 4/1982 | Grollier et al. | 252/174.17 |

FOREIGN PATENT DOCUMENTS 2901070 7/1979 Fed. Rep. of Germany .
2421605 12/1979 France .

*Primary Examiner*—Paul Lieberman
*Assistant Examiner*—Hoa Van Le
*Attorney, Agent, or Firm*—McAulay, Fields, Fisher, Goldstein & Nissen

[57] ABSTRACT

A detergent composition for cleaning hair and skin is a mixture of:
(a) a major amount of one or more oils of the group comprising mineral, vegetal, animal and synthetic oils, and
(b) a minor amount of at least one emulsifying agent, preferably a mixture of emulsifying agents, one of which is a saccharose ester, whereby cleaning action is improved while a protecting lipid layer is left onto the skin. The composition may also contain a bentonite or montmorillonite clay to improve the hydrating and restoring effects thereof.

21 Claims, No Drawings

DETERGENT COMPOSITION

This application is a continuation of application Ser. No. 709,508, filed Mar. 8, 1985, which is a continuation-in-part of application Ser. No. 628,149, filed July 5, 1984, both now abandoned.

FIELD OF THE INVENTION

The present invention relates to a detergent composition for the hair and skin and, more specifically, to a detergent composition which is essentially non irritating and capable of maintaining the skin smooth and soft.

The mechanism of the skin detersion is well known and has been extensively studied: this problem has been treated always by using chemical compounds having specific detergent action.

Since a detergent action, more or less strong but nevertheless specific, is accompanied by not negligible side effects, such as, for instance, some dryness of the skin, combined with phenomena like chaps, roughness, and blushing, and since these problems have not only an aesthetic effect but also involve more generally the natural defences of the skin, a great number of attempts has been suggested and tried thoughout the years, the use of complex formulations these besides a component having specific detergent action contain other ingredients, such as for example emollient substances capable or reducing skin roughness as induced by the detersion. As typical example, lanolin and other animal, vegetal or mineral oils can be cited, which are present in minor amounts in detergent compositions.

Another common expedient is that of adjusting the pH of a cleaning composition by making it nearly neutral.

The use of oily mixtures for skin and hair care, both for detergent and for cosmetic purposes already has been proposed.

These compositions were applied by rubbing on the skin and/or the hair and then were removed.

The composition also could be added with a surface active agent or an emulsifying agent, in order to promote the removal of the composition by rinsing with water.

In summary, the prior art taught the application of these compositions to the skin and/or the hair by rubbing, maintaining the composition into contact with the skin and/or the hair for a predetermined time of some minutes or more, and thereafter rinsing with water, taking advantage of the fact that the presence of an emulsifying agent causes an emulsion to be formed by which the composition is more easily removed.

Pediatrists use oily compositions with which the body is rubbed in areas covered by absorbing napkins, etc. in order to counterweight the macerating effect of the body liquids, and of feces. It is known also that baby skin is too delicate to stand the detergent action even of very mild soaps.

In this connection it is worth to shortly resume the properties and main features of the lipid film or of the sebum coating the skin. It is a hydrophilic, homogeneous, finely emulsified layer having important protecting functions.

A lipid film is generated, in varying amounts and composition, throughout the life of the human directly onto the surface of the skin by sebaceous glands.

Some times the sebum production is in excess with respect to the need of the skin (seborrhea) or is insufficient (alipic skin). In both cases disorders, anomalies, alterations and cutaneous defects are induced; thus the importance of the sebum and of its biological role can be appreciated.

Sebum as a matter of fact protects the skin from atmospherical pollutants, from cutaneous steeping, from the dehydration and from temperature variations. Moreover it acts as a surface shield against chemically aggressive substances, hindering their contact with the skin and their absorption. It acts also as a carrier for the precursors of vitamin D and has an important anti-infective activity against several pathogenic micro-organisms.

Lastly sebum has a lubricating, emollient and lenitive effect, thus inducing skin sofness and turgidity and preventing an excessive evaporation of surface water. Sebum is an semisolid lipid mixture consisting of triglycerides, free fatty acids, waxes, sterols and related esters, alcohols and hydrocarbons (a typical example in squalene) together with non negligible amounts of vitamins (mainly provitamin D and vitamins A and E).

Sebum, owing to the presence therein of cholesterol and of its esters, produces a water/oil emulsion, which although being capable of including relevant amounts of water, maintains its lipidic, non-hydrodispersible character, so that it can not be removed from the skin with the help of water alone.

Skin cleaning means the removal of sebum, of waste and of dirt, but is not a physiological operation since it also means removal of the lipidic protective layer.

Skin cleaning is however a necessary operation since not only dirt and wastes are to be removed, but also a portion of the surface sebum layer, namely the older one as regards it formation, must be removed. In fact, sebum, some time after its generation, undergoes chemical changes, owing to both oxygen in the air and to microorganisms normally present in the skin, these changes making the sebum irritating for the skin.

There is this need for means capable of efficiently removing from skin wastes, dirt and the surface portion of the sebum, without fully removing the sebum layer, and without irritating the skin.

It is noteworthy to remark that like the soaps and detergent compositions, the so called cleansing milks are not suitable, since their cleaning action is not sufficient, to remove the surface part of the sebum, and heavy make up or dirt.

SUMMARY OF THE INVENTION

The composition according to the present invention solves the above the above mentioned problems and to this end consists in a mixture comprising:
 (a) a major amount of at least one oleagenous material selected among mineral, vegetal, animal and synthetic oils and mixtures thereof, and a minor amount of:
 (b) an emulsifying mixture of at least two emulsifying agents, soluble in the oily component (a) and one of which is a saccharose ester.

As already indicated one of the essential component of the compositions of the present invention is an oil or a mixture of vegetal, mineral or animal oils. As examples of oils useful in the present invention, the following can be cited.

As mineral oils:
Vaseline oil, silicone oil and mixtures thereof
As vegetal oils:

almond oil, mais oil, olive oil, walnut oil, soya oil, grape-stone oil, sesame oil, peanut oil, coconut oil, avocado oil, sunflower oil and mixtures thereof, As animal oils:

Turtle oil, mink oil, marmot oil, lanoline oil.

Among synthetic oils, those already known in the cosmetic field can be used, such as, for instance, isopropyl miristate, palmitate and stearate, octyldecanol, decyl oleate, derivatives of isostearic acid, diisopropyladipate, miristyllactate and mixtures thereof. As a total or partial substitution for the oil vegetal gelatine can be used and, in that case, the density of the detergent composition of the invention can also be adjusted.

The amount of the oleagenous material or of the oil mixture in the subject composition varies between 80 and 98% by weight and is preferably of the order of 90%.

Another essential component of the compositions according to the invention is an emulsifying mixture soluble in the subject oils, selected among anionic, cationic, non ionic and ampholecic emulsifiers and mixtures thereof. Specific examples of emulsifiers useful in the compositions of the present invention comprise:

fatty alcohol sulphates and derivatives;
quaternary ammonium compounds and derivatives;
derivatives of aminoacids, betaine and the like;
fatty acids and alcohols condensed with ethylene oxide;
polyethylene and polyoxypropylene derivatives and mixtures thereof.

As is well known emulsifying agents have no specific detergent action so that it is totally unexpected that the combination of an oil and of an emulsifying substance have detergent action. The most surprising feature is that this combination acts as s soap when combined with water before it is applied to the skin and is able to leave a lipid layer onto the skin which means that only a portion of the sebum layer is removed.

The subject emulsifiers are in turn contained in the composition of the invention in a percentage by weight of between 2 and 20%.

According to a further feature of the invention a minor amount of the emulsifiers can be replaced by a conventional surface active agent.

In this connection it is however to be pointed out that, in comparison with the major amount of the oily component, the small amount of surface active agent probably is responsible of the detergent action.

According to a feature of the present invention, is foreseen of a saccharose ester is one of the emulsifying agents. These exert a synergistic effect with the emulsifying agents present in the composition. The resulting emulsion is finer, softer and more flowable.

This fact has been demonstrated by tests carried out with a composition of the present invention, namely comprising an oily part and an emulsifying agent, by adding a saccharose ester selected among: saccharose monolaurate, monopalmitate, monosterate and distearate, the saccharose ester being added in the amount of 0.5% by weight of the composition.

The control composition contained 72% of mineral oil, 25% of soya oil and 3% of polyoxythyleneoleyl ether.

The results are reported in the following table as the transparency T of the resulting emulsion at 650 nm and for several grades of dilution.

| | T at 650 nm | | |
|---|---|---|---|
| | dilution 1:1000 | dilution 1:2500 | dilution 1:5000 |
| Control sample (without saccharose ester) | 48.8 | 78.9 | 81.6 |
| Sample with saccharose monolaurate | 30.4 | 62.5 | 75.0 |
| Sample with saccharose monopalmitate | 23.5 | 55.4 | 74.2 |
| Sample with saccharose monostearate | 26.3 | 58.8 | 76.0 |
| Sample with saccharose-distearate | 22.0 | 50.3 | 75.5 |

As it can be appreciated from the values of transmittance, in all cases, the addition of saccharose esters increases turbidity of the oil/water emulsion which in turn increases the milky consistency and thus the detergent action.

The concentration of the saccharose ester can vary between 0.05 and 2% by weight relative to the weight of the composition.

According to a further feature of the present invention, powdered clay of bentonite or montomorillonite type is added: in fact it has been found that by such an addition the thickness of the lipid layer remaining on the skin after the rinsing with water can be controlled.

More particularly if the amount of the clay powder present in the composition is of between 0.5 and 1.5% by weight a more consistent thickness of the lipid layer is obtained, which makes the skin superfat, whereas if the content of clay powder is of between 1.5 and 10%, a creamy layer remains onto the skin.

Otherwise stated, if the content of clay powder present in the composition is in the above lower range the skin feels soft and a little greasy, whereas if the content is in upper range the skin appears as when a cream layer is applied. According to a further feature of the invention the compositions of the present invention are also endowed with skin hydrating and restituting properties, as well as with nutrient and revitalizing functions.

For a hydrating and restituting action the composition can be malified with hydrating agents, such as, for instance, glycerin, urea and aminoacids which are very poorly or not soluble and not dispersible in the oils, by which skin dehydration, as caused by the removal of natural hydrating substances as induced by the detergent action, is prevented.

As regards the aminoacids, valine, isovaline, leucine and isoleucine cited are preferred.

Their presence together with urea and glycerine gives a revitalizing action, whereas to get a nutrient effect a liposoluble vitamin (such as vitamin A, E or F) is added.

According to a further feature of the invention, the subject compositions are used as hair shampoo instead of known shampooing compositions, the latter always causing the removal from the scalp and from the hair of an excess of protecting sebum, whereby a so-called reactive seborrhea is induced, which becomes worse if the washing frequency is increased.

The use of the compositions of invention as hair shampoos prevents the reactive seborrhea from occurring both because the conventional detergents are absent and because a hydrolipidic sebum-like film remains in the place of the removed natural sebum.

In this connection it is noteworthy to resume the properties of the compositions of the present invention; thus, these do not change. They are:
- the skin pH;
- fully tolerated by the skin with no irritating action towards the eyes and the mucosae:
- do not cause allergic or photosensitizing effects;
- permit the removal from the skin of all types of residues, e.g. fatty make up;
- induce the removal of only the surface part of the sebum, namely that which possibly has undergone the greater alterations; these compositions:
- leave no unpleasant residues on the skin;
- the epicutaneous lipidic layer is not strongly attacked, whereby the skin is safeguarded from blushing desquamation and the like.

As an explanation of the favourable results of the compositions of the present invention, which however should not be considered as exhaustive or limiting, it is to be taken into account that the subject compositions form a milky emulsion in the presence of water, most of which is of the type oil/water, and is thus washable, whereas a small proportion is of the opposite type (namely water/oil emulsion): the latter portion remains on the skin after rinsing, thus producing a protective effect. In fact this layer substitutes for the sebum portion which is removed, retaining its more important chemico-physical and biological properties, and being at the same time more stable towards oxidizing agents and more resistant to attack by microorganism.

Some examples of formulation of the compositions of the invention are given hereinafter:

EXAMPLE 1
| | |
|---|---|
| mineral oil | 90% |
| polyoxyethyleneoleyl ether | 10% |

EXAMPLE 2
| | |
|---|---|
| mineral oil | 95% |
| polyoxyethyleneoleyl ether | 5% |

EXAMPLE 3
| | |
|---|---|
| animal oil | 90% |
| ethoxylated lanoline | 8% |
| sodium lauryl ether sulphate | 2% |

EXAMPLE 4
| | |
|---|---|
| mineral oil | 40% |
| vegetal oil | 40% |
| perhydrosqualene | 10% |
| polyethyleneglycol stearate | 5% |
| amphoteric surface active agent | 5% |

EXAMPLE 5
| | |
|---|---|
| glyceryl tricaprilate | 48.9% |
| Isopropyl miristate | 48.3% |
| Cholesterol condensed with ethylene oxide | 2% |
| Saccharose monopalmitate | 0.2% |
| antioxidant and perfume | enough |

EXAMPLE 6
| | |
|---|---|
| mais oil | 46.8% |
| grape-stone oil | 0.2% |
| polyoxyethyleneoleylether | 4% |
| glycerylmonostearate | 0.2% |
| sorbitan monolaurate | 2% |
| saccharose distearate | 0.1% |
| antioxidant and perfume | enough |

EXAMPLE 7
| | |
|---|---|
| mineral oil | 58.4% |
| sunflower oil | 25.05% |
| lanoline oil | 10% |
| poly-ethyleneglycol stearate | 1.5 |
| polyoxyethyleneoleylether | 3% |
| saccharose monolaurate | 0.05% |
| bentonite | 2% |
| antioxidant and perfume | enough |

EXAMPLE 8
| | |
|---|---|
| sweet almond oil | 44.8% |
| olive oil | 44.8% |
| polyoxyethyleneoleylether | 5% |
| spermaceti | 0.2% |
| bees wax | 0.2% |
| cethyl alcohol condensed with ethylene oxide | 4% |
| cetyl lactate | 3% |
| saccharose monolaurate | 1% |
| bentonite | 3% |
| perfume | enough |

EXAMPLE 9
| | |
|---|---|
| hydrogenated coconut oil | 36.5% |
| isopropylpalmitate | 36.5% |
| polyethylene-polypropylene glycol | 10% |
| glyceryl tricaprilate | 5% |
| stearyl alcohol condensed with ethylene oxide | 4% |
| cetyl lactate | 3% |
| saccharose monolaurate | 1% |
| perfume | enough |

EXAMPLE 10
| | |
|---|---|
| diisopropyl adipate | 38.75% |
| isostearyl alcohol | 38.75% |
| decyl oleate | 10% |
| sorbitan monostearate | 1.5% |
| poly-oxyethylenelauryl alcohol | 2% |
| poly-oxyethyleneoleyl alcohol | 4% |
| montmorillonite | 5% |
| antioxidant and perfume | enough |

EXAMPLE 11
| | |
|---|---|
| 70% vaseline oil | 54.11% |
| 30% sesame oil | 23.19% |
| octyl dodecanol | 10% |
| glycerin | 5% |
| urea | 0.5% |
| polyoxyethyleneoleylether | 6% |
| saccharose monopalmitate | 0.2% |
| antioxidant and perfume | enough |

EXAMPLE 12
| | |
|---|---|
| lanoline oil | 7.8% |
| mink oil | 5% |
| marmot oil | 5% |
| avocado oil | 5% |
| glycerine | 5% |
| urea | 1% |
| aminoacids with aliphatic chain having a content of carbon atoms greater than 4 | 1% |
| saccharose monostearate | 0.2% |
| bentonite | 5% |
| ethoxylated lanoline | 2% |
| poly-oxyethylenelauryl ether | 5% |
| poly-oxyethylenelauryl ether | 5% |
| antioxidant and perfume | enough |

EXAMPLE 13
| | |
|---|---|
| 50% isostearyl alcohol | 36.2% |
| 50% isopropyl miristate | 36.2% |
| corn germ oil | 10% |
| perhydrosqualene | 5% |
| sorbitan hexaoleate | 2% |
| poly-oxyethylenesorbitan monolaurate | 3% |
| poly-oxyethylenesorbitan monostearate | 3% |
| bentonite | 1% |
| saccharose monolaurate | 0.1% |
| glycerin | 3% |
| urea | 0.5% |
| antioxidant and perfume | enough |

EXAMPLE 14
| | |
|---|---|
| vaseline oil | 30% |
| isopropylmiristate | 32% |
| castor oil | 29% |
| poly-oxyethylenelauryl alcohol | 8% |
| saccharose laurate | 1% |

EXAMPLE 15
| | |
|---|---|
| isostearyl isostearate | 36% |
| soya oil | 54% |
| sorbitan monopalmitate | 2% |
| poly-oxyethylene oleylstearate | 4% |
| sorbitan trioleate | 4% |

-continued

| | EXAMPLE 16 |
|---|---|
| lanoline oil | 10% |
| silicon oil | 5% |
| olive oil | 30 |
| soya oil | 38% |
| isopropyl adipate | 5% |
| octyldodecanol | 5% |
| polyoxypropylene stearyl alcohol | 5% |
| polyoxypropylene stearyl alcohol | 4% |
| polyoxyethyelene sorbitan monooleate | 3 |

The above last three examples disclose shampooing compositions.

I claim:

1. A detergent composition for cleaning hair and skin, consisting essentially of a major amount of an oleaginous material selected from the group of animal, vegetable, mineral and synthetic oils and mixtures thereof, 2.0 to 20 percent by weight of a mixture of at least two emulsifying agents, one of said agents being 0.05 to 2.0 percent by weight of a saccharose ester; and the optional presence of a hydrating agent, a vitamin and a powdered clay, from 0 percent of the hydrating agent; 0 percent of the vitamin and 0 percent of the powdered clay.

2. Detergent composition according to claim 1, wherein said oil consists of a mixture of oils.

3. Detergent composition according to claim 1, wherein said oleaginous material is present in an amount of 80 to 98% by weight of said composition.

4. Detergent composition according to claim 1, wherein said other emulsifying agent is selected from the group consisting of anionic, cationic, non-ionic and amphoteric emulsifying agents.

5. Detergent composition according to claim 4, wherein said emulsifying agent is selected among:
   fatty alcohol sulphates and derivatives;
   derivatives of amonoacids and betaine;
   fatty acids and alcohols condensed with ethylene oxide;
   saccharose esters; and
   polyethylene and polypoxypropylene derivatives and mixtures thereof.

6. Detergent composition according to claim 1, wherein said oleaginous material is selected among vaseline oil and silicone oil.

7. Detergent composition according to claim 1, wherein said vegetable oil is selected from the group of almond oil, mais oil, olive oil, walnut oil, soya oil, grape-stone oil, sesame oil, peanut oil, coconut oil, avocado oil, sunflower oil, corn oil and mixtures thereof.

8. Detergent composition according to claim 1, wherein said animal oil is selected from the group of turtle oil, mink oil, marmot oil and lanoline oil.

9. Detergent composition according to claim 1, wherein said saccharose ester is selected from the group of saccharose mono- and di-laurate, mono- and di-palmitate, mono- and distearate and mixtures thereof.

10. Detergent composition according to claim 1, further containing a hydrating agent.

11. Detergent composition according to claim 10, wherein said hydrating agent is selected from the group of glycerin, urea and aminoacids, non-dispersible and non- or poorly soluble in water, said agent being present both alone and in combination.

12. Detergent composition according to claim 11, wherein said aminoacids are selected from the group of valine, isovaline, leucine, isoleucine and mixtures thereof.

13. Detergent composition according to claim 1, further containing a vitamin selected from the group comprising vitamins A, E and F and mixtures thereof.

14. Detergent composition according to claim 1, further containing powdered clay.

15. Detergent composition according to claim 14, wherein said clay is selected from the group of bentonite, montmorillonite clays and mixtures thereof.

16. Detergent composition according to claim 14, wherein said clay is present in an amount of 0.5 to 10% by weight of said composition.

17. Detergent composition according to claim 16, wherein said clay is present in the amount of 0.5 to 1.5% by weight of said composition.

18. Detergent composition according to claim 16, wherein said clay is present in the amount of 1.5 10% by weight of said composition.

19. Detergent composition according to claim 1, wherein said synthetic oil is selected from the group of isopropyl miristate, palmitate and stearate, octyl dodecanol, decyl oleate, derivatives of isostearic acid, diisopropylapidate, miristyl lactate and mixtures thereof.

20. A detergent composition consisting essentially of from 80 to 98 percent by weight of an oleaginous material selected from the group of animal, vegetable, mineral, synthetic oils and mixtures thereof; and
   2.0 to 20 percent by weight of a mixture of at least two emulsifying agents the first said emulsifying agent being 0.05 to 2.0 percent by weight of a saccharose ester; and 0.5 to 10.0 percent of powdered clay.

21. A skin and hair cleaning method comprising applying a composition according to claim 1 to the hair or skin and removing said composition by rinsing with water.

* * * * *